United States Patent [19]

Tansill

[11] 4,272,898
[45] Jun. 16, 1981

[54] RESIN-COATED FIBER MASS CONTAINING CATALYST-FILLED HOLLOW FIBERS

[76] Inventor: Horace A. Tansill, Box 278, Santa Barbara, Calif. 93102

[21] Appl. No.: 929,257

[22] Filed: Jul. 31, 1978

Related U.S. Application Data

[60] Division of Ser. No. 665,805, Mar. 11, 1976, Pat. No. 4,128,951, which is a continuation of Ser. No. 412,581, Nov. 5, 1973, abandoned.

[51] Int. Cl.$^3$ .................. A43B 13/38; A61F 5/04
[52] U.S. Cl. .................................. 36/44; 36/71; 128/90; 206/219; 264/313; 428/376; 428/397; 428/398
[58] Field of Search .................. 36/44, 43, 71, 88; 128/90; 206/219; 264/313, 223; 428/376, 397, 398

[56] References Cited

U.S. PATENT DOCUMENTS

| | | | |
|---|---|---|---|
| 2,864,492 | 12/1958 | Lappala | 128/90 |
| 3,043,424 | 7/1962 | Howard | 206/219 |
| 3,100,045 | 8/1963 | Via | 206/219 |
| 3,121,431 | 2/1964 | Rosenhaft | 128/595 |
| 3,227,795 | 1/1966 | Ingersoll | 264/223 |
| 3,302,410 | 2/1967 | McLean | 206/219 |
| 3,309,447 | 3/1967 | Wegley | 264/313 |
| 3,631,854 | 1/1972 | Fryer | 128/90 |
| 3,674,134 | 7/1972 | Turner | 206/219 |
| 3,705,646 | 12/1972 | Jankowski et al. | 206/219 |
| 3,722,833 | 3/1973 | Inoue et al. | 206/219 |
| 3,728,206 | 4/1973 | Buese | 128/90 |
| 3,736,673 | 6/1973 | Dubner | 36/44 |
| 3,737,027 | 8/1971 | Ball | 206/219 |
| 3,756,388 | 9/1973 | Murphy | 206/219 |
| 3,830,475 | 8/1974 | Inoue | 206/219 |
| 3,861,522 | 1/1975 | Llewellyn et al. | 206/219 |
| 3,908,644 | 9/1975 | Neinart et al. | 128/90 |
| 3,925,277 | 12/1975 | Lampe | 206/219 |
| 3,990,437 | 11/1976 | Boyden et al. | 428/398 |
| 4,019,630 | 4/1977 | Plaisted | 206/219 |
| 4,060,075 | 11/1977 | Blooner et al. | 128/90 |

FOREIGN PATENT DOCUMENTS

7413100   4/1974   France .................................. 128/90

Primary Examiner—W. E. Hoag
Attorney, Agent, or Firm—Lyon & Lyon

[57] ABSTRACT

A moldable article useful for making a form-stable article is described. The moldable article comprises a formable material that is a moldable polymeric or prepolymeric substance that can be cured to a form stable state and a curing agent, in close proximity to the curable substance but isolated therefrom, in frangible hollow fibers. In use, the frangible hollow fibers are ruptured to release the curing agent and the moldable article, in a first configuration, can be shaped to a second configuration in which it is maintained until the formable material is cured sufficiently for it to be form-stable in the second configuration. The moldable article can be used to make molds, casts, support for a portion of the human or animal anatomy, or other articles with diverse utilities.

7 Claims, 21 Drawing Figures

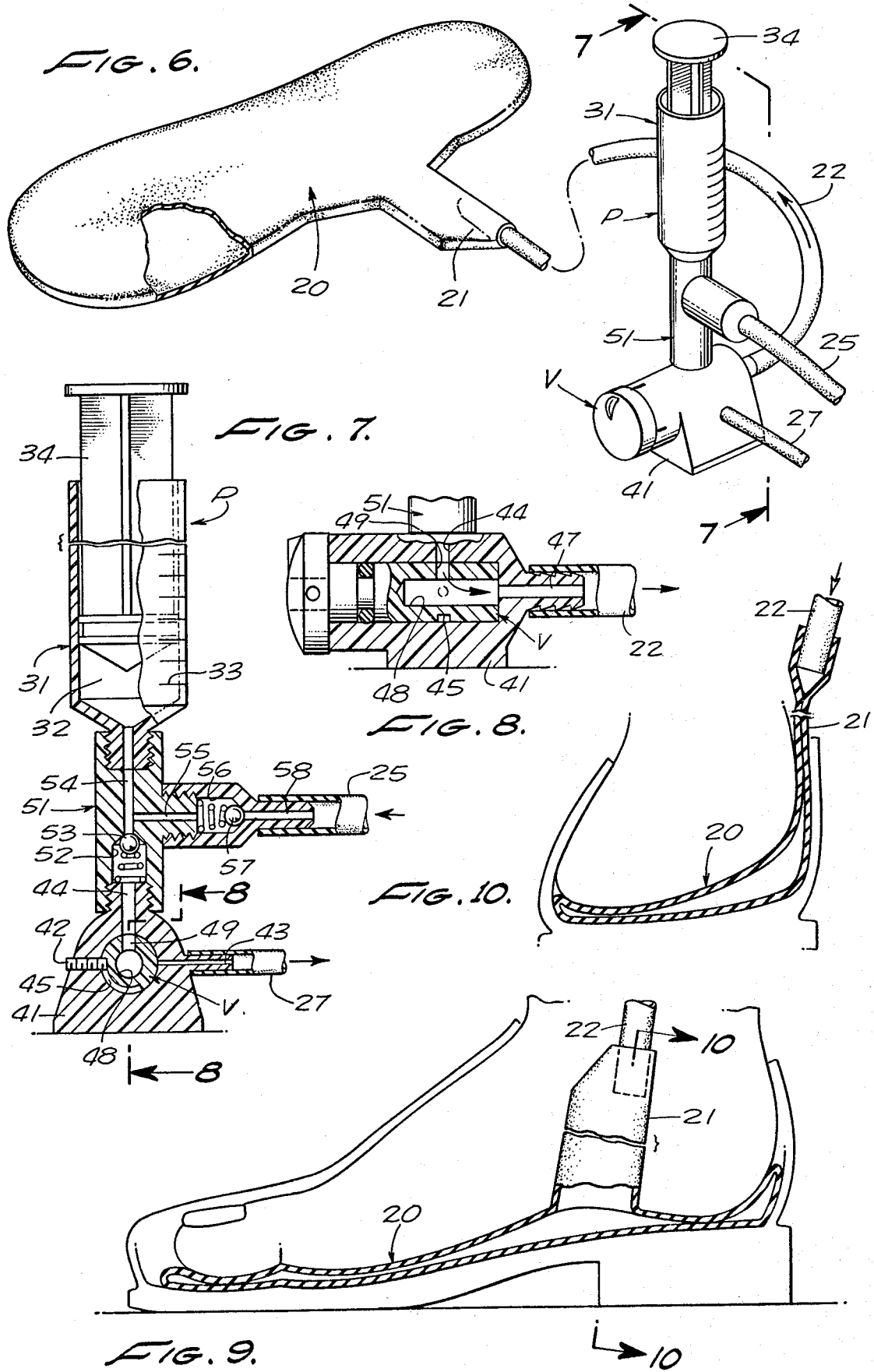

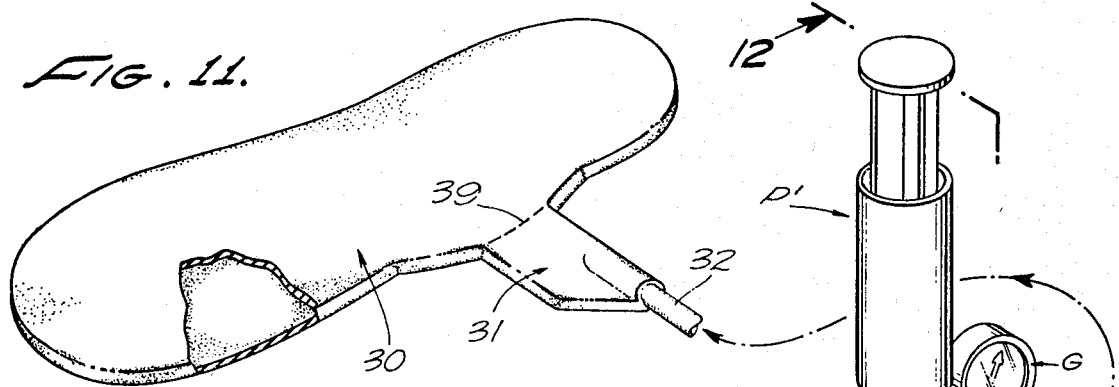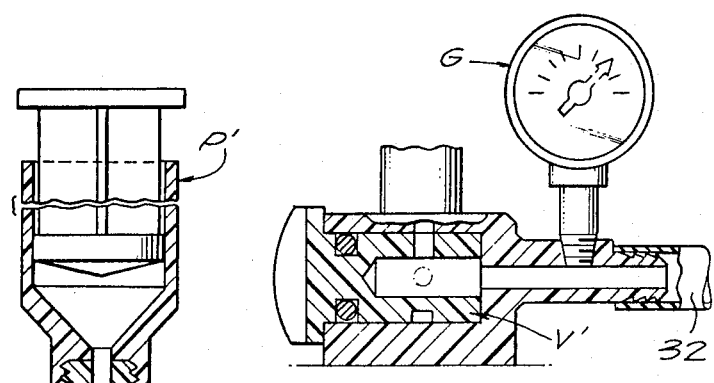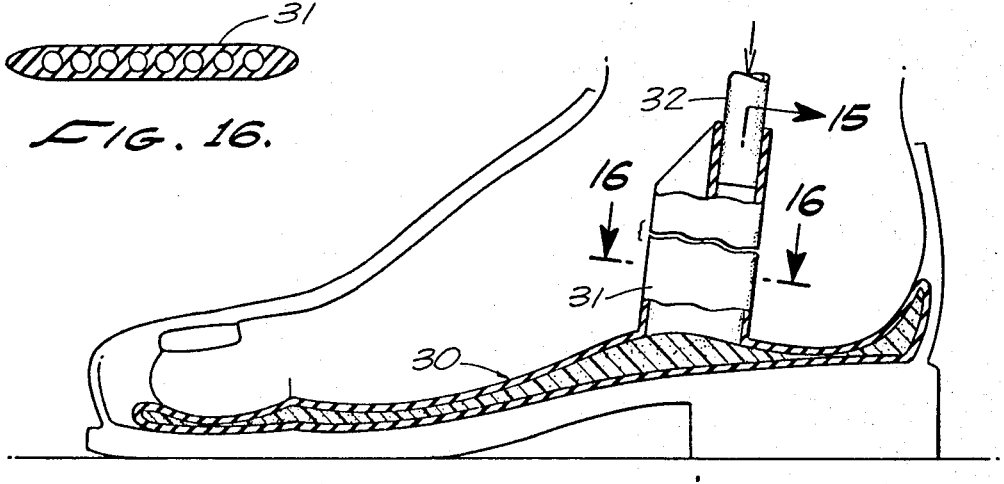

RESIN-COATED FIBER MASS CONTAINING CATALYST-FILLED HOLLOW FIBERS

CROSS-REFERENCE TO RELATED APPLICATIONS

The present application is a division of my copending U.S. patent application Ser. No. 665,805, filed on Mar. 11, 1976, which is a continuation of application Ser. No. 412,581, filed Nov. 5, 1973 Application Ser. No. 665,805 is now U.S. Pat. No. 4,128,951 and application Ser. No. 412,581 is now abandoned. The disclosure of each of these is incorporated by reference.

BACKGROUND OF THE INVENTION

There are many applications for articles which, in a first form, are easily shaped or molded to a second form in which the article is form stable. This application relates generally to such articles.

The use of casts, fabricated from plaster of paris and like substances, and contoured to the portion of a body for which they are designed to lend support is well-known. Such casts are typically fabricated by methods involving the use of a mixture of plaster of paris and water or other suitable material.

The use of molds and casts for taking impressions of a variety of tangible objects or forms, such as, for example, models, tooth cavities, machine parts and decorative plaques are well-known.

Such molds and casts are ordinarily fabricated by simply pouring the plaster of paris and water mixture or other material into an impression or around the article to be molded and thereafter allowing said mixture to cure. Alternatively, a room temperature vulcanized (RTV) silicon rubber liquid can be mixed with a suitable catalyst and poured over the article for which a mold is desired. When the rubber is cured, it can be separated from the object and used as a mold of the object.

More recently, curable polymeric materials have been used to prepare, in situ, the padding for ski-boots, in effect making each pair a custom made item since the curable material conforms to the leg of the owner.

The use of removable arch supports in shoes is also well-known. Such arch supports are manufactured in standard sizes and shapes, typically by using several layers of leather and selecting each piece of leather as to size and configuration so that the composite structure assumes the desired shape.

Custom-made arch supports that are removable from the shoe are likewise well-known. A measurement technique is employed, such as by making an impression of the bottom of the foot and then fabricating the arch support accordingly.

The procedures for fabricating molds, splints, braces and casts for tangible forms such as, for example, chess pieces, decorative plaques, portions of the human body or any of other myriad purposes, heretofore available however, have left much to be desired. Likewise, the procedures for fabricating arch supports, heretofore available have left much to be desired.

The methods for fabricating such molds, splints, braces and casts for the purposes hereinbefore described involve an untidy procedure and a great deal of difficulty and time in completing the same.

With respect to the arch supports, ready-made products generally do not fit very well, while the custom-made products involve a great deal of difficulty, time, and expense in completing their fabrication.

An object of the present invention is to provide a readily moldable article which, after molding, is form stable.

Another object of the present invention is to provide a means for making articles of unusual shape or configuration.

Another object and purpose of the present invention, therefore, is to provide a method for preparing molds, casts, splints, prosthetic devices or braces for the purposes as hereinbefore explained, and custom made machine castings, decorative plaques, ski boot padding, arch supports or shoe inserts, and the like which will be a tidier and more simple procedure. Insofar as devices to be worn by humans are concerned, the method provides devices with a high degree of comfort for the wearer. The method can also be carried out with a minimum of time or expense.

SUMMARY OF THE INVENTION

The invention, though being of general application to a variety of uses and having numerous tangible forms, as will be described herein, will, however, for the purpose of illustrating the invention, be initially explained with specific reference to a custom-formed shoe insert.

In accordance with the present invention a container having flexible upper and lower walls is filled with a formable material that is capable of curing at about room temperature to form a form-stable material, and the container is inserted in the shoe beneath the bottom of the foot. Preferably, the formable material is a polymeric or prepolymeric material that yields an elastomer or other polymeric material when cured and an appropriate curing agent. Appropriate pressure is applied downwards on the foot while the formable material is curing. The end result is a shoe insert whose upper surface precisely fits the bottom of the foot of the wearer, while its lower surface precisely fits the inner shoe surface.

Generally, the invention comprises the provision of a preformed prosthetic blank which is at least substantially closed and the walls of which are composed generally of flexible barriers. The prosthetic blank is configured in the form of a blank unformed arch support and is adapted to be inserted in a shoe and subjected to an in situ molding process for the purpose of producing a prosthetic foot device in situ. The structural shape of the prosthetic foot device is determined by providing within the interior of the prosthetic blank a curable but initially moldable material.

In one form the material which is to be cured to provide the necessary resilient structural rigidity for the prosthetic device is incorporated within the prosthetic blank at the time of manufacture. In the configuration where the prosthetic blank, as supplied to the customer, contains moldable material within it, there is generally included within the closed walls of the prosthetic blank a curable pre-elastomeric material and a catalyst or cross-linking agent suited for curing the pre-elastomeric material as well as other conventional materials such as, for example, fillers, sponge rubber or cork granules, foaming agents, and the like. The catalyst or cross-linking agent is separated from the polymeric material by a barrier of a material which is, or readily rendered, frangible and thus is easily broken through suitable manipulation of the prosthetic blank to initiate a polymerization reaction.

In the configuration where the prosthetic blank contains no polymeric or prepolymeric material, as supplied to the customer, provisions are made for injecting this material into the prosthetic blank at the time of use. The prosthetic blank must first be squeezed flat or otherwise evacuated so as to remove air bubbles from within the interior of the closed prosthetic blank. Evacuation is followed by the introduction of a suitable premixed polymeric admixture which then polymerizes in situ. In situ molding is accomplished by inserting the prosthetic blank into a preselected shoe or, in another form of the invention, into a ski boot. In the case of a prosthetic device, the intended wearer of the shoe then inserts his foot into the shoe on top of the prosthetic blank. The polymerizable reaction admixture which is provided in the prosthetic blank is allowed to polymerize while the wearer of the shoe applies appropriate pressure on the prosthetic device by standing or by pressing his foot against an appropriate surface. Preferably, pressure is applied by seating the customer and placing weights on his knees, for example, by using sandbags of appropriate weight. By applying less than the customer's full weight on the blank, the foot is incompletely flattened. As a result, the device in its cured state conforms to the incompletely flattened foot. Therefore, support is provided the arch when the customer's full weight is brought to bear on the foot.

The cured final shape of the prosthetic device is determined in some substantial part by the amount of pressure applied during the in situ molding, with the arch being depressed to a flatter profile by increasing the pressure on the prosthetic device during the molding operation. The molding is continued for a period of time sufficient to permit the polymerizable reaction admixture to set to a resiliently rigid condition such that changes or alteration in pressure will not substantially alter its shape.

Curing should be accomplished at approximately room temperature or, in any event, at a temperature such that the wearer of the shoe will not experience any discomfort during the molding process. Also the nature of the curable admixture should be such that it does not generate a great deal of exothermic heat during the polymerization reaction. Suitable polymerizable reaction admixtures are well-known and include for example, room temperature vulcanizing (RTV) silicone rubber forming admixtures, and the like. Such materials are available from, among others, the Dow Corning Company.

When the procedure is followed where the prosthetic blank is first evaluated and then the curable admixture is injected into the void defined by the walls of the prosthetic blank, suitable equipment is provided which preferably accomplishes both the evacuation and the injection without subjecting the wearer of the shoe to long delays. A product resulting from this in situ molding process is a custom made prosthetic foot device which is precisely contoured to the upper surface of the individual shoe's sole and the bottom of the individual wearer's foot.

According to one mode of practicing the invention, the flexible container is evacuated and filled with formable material and is sealed before being inserted into the shoe. A downward pressure on the foot, preferably of a constant value, is maintained as previously described while the formable material is curing. The shoe insert is then complete and ready for use. Accordingly to this first mode of practicing the invention, the amount of formable material that is contained inside the flexible container has to be determined or selected before actually fitting the shoe insert to the foot and shoe of the wearer. The selection process may be accomplished in two different ways.

One way is to choose an empty container having an opening, make a measurement from the foot and the shoe of the customer to determine the amount of filler material that is needed, and then after evacuating air to insert this amount of material into the container and close and seal the container.

Another way of achieving the desired result is to prepare ready-made containers of various shoe sizes and arch void sizes each of which has a predetermined amount of filler material inside. A particular container to be used for a particular customer may then be selected on the basis of the size and shape of the container and the quantity of filler material which it contains. Where ready-made containers are being used, it is necessary to control the initiation of the curing of the filler material. A filler material may be used which is normally in a liquid state but when exposed to a curing agent will cure to a resilient permanent state. The quantity of curing agent that is needed may be quite small. In one embodiment the catalyst is placed inside a bulb, or inner container, that is of frangible construction. Prior to placing a shoe insert inside the shoe it is then necessary to exert pressure on the flexible container at the spot where the bulb or inner container is located, in order to fracture the bulb and thereby release the curing agent, and then the container is kneaded to intimately mix the curing agent and filler materials.

To better distribute the curing agent throughout the formable material, and reduce or eliminate the need for kneading the article to achieve distribution of the curing agent, the agent may be contained in plural small frangible containers positioned throughout the flexible outer container rather than in a single container. The plural containers are preferably uniformly distributed throughout the curable material. The plural containers may take the form of small spheres or be elongate tubular structures. In yet another form of the invention, the curable material and curing agent may be arrayed in alternating layers separated by frangible barriers.

When preformed, it is expected that the moldable article will be shipped to the use. This prevents the opportunity during handling for premature rupture of the frangible containers that separate the curing agent from the curable material. In a particularly preferred embodiment of the present invention, the frangible container is initially formed of a pliant material capable of being rendered frangible by the user. Materials suited to this end are partially cross-linked materials that can be further embrittled by additional cross-linking when exposed to heat, ionizing radiation, microwave radiation, ultrasonic aging, pressure or other suitable initiators.

When the article is formed using a relatively flexible prefrangible material to encase the curing agent, the article can be handled without fear of rupturing the container holding the curing agent until the operation which renders the material frangible is performed.

According to a second mode of practicing the invention the evacuated empty container is filled at the same time it is being fitted to the foot. The empty container is placed within the shoe beneath the foot of the wearer or customer. Then an appropriate amount of formable material is inserted through the opening into the interior of the container. Sufficient pressure is placed on the formable material to fill the container. As before, appropriate weight is then maintained on the foot until the formable material has cured.

DRAWING SUMMARY

FIG. 6 is a perspective view of a measuring apparatus provided in accordance with the present invention;

FIG. 7 is a cross-sectional elevational view taken on the line 7—7 of FIG. 6;

FIG. 8 is a fragmentary cross-sectional view taken on the line 8—8 of FIG. 7;

FIG. 9 is an elevation view, partially in cross-section, of the foot and shoe of the wearer when the measuring apparatus of FIG. 6 is being used;

FIG. 10 is a transverse cross-sectional view taken on the line 10—10 of FIG. 9;

FIG. 11 is a perspective view of a custom-filled shoe insert together with the apparatus for filling it;

FIG. 12 is a cross-sectional elevation view taken on the line 12—12 of FIG. 11;

FIG. 13 is a fragmentary cross-sectional view taken on the line 13—13 of FIG. 12;

FIG. 14 is an elevation view, partially in cross-section, of the insert of FIG. 11 when inserted in the shoe of the wearer;

FIG. 15 is a transverse cross-sectional view taken on the line 15—15 of FIG. 14;

FIG. 16 is a fragmentary cross-sectional view taken on the line 16—16 of FIG. 14;

DESCRIPTION OF THE PREFERRED EMBODIMENT

Figure 1:
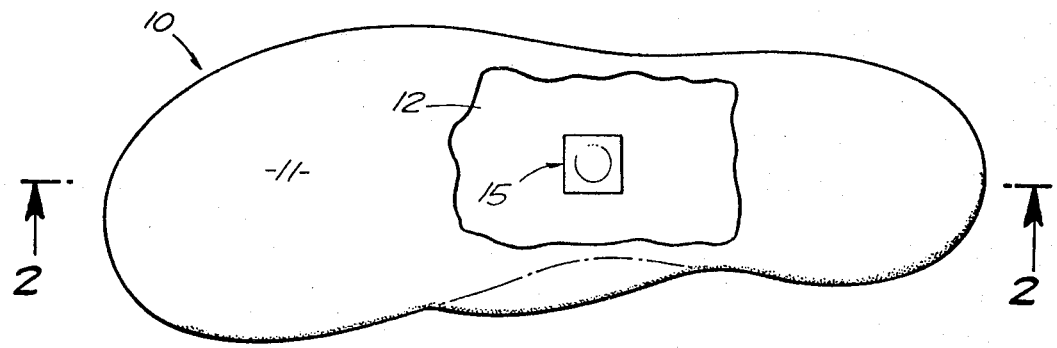
FIG. 1 illustrates one embodiment of the present invention and specifically, a top plan view of a ready-made shoe insert.
Figure 2:
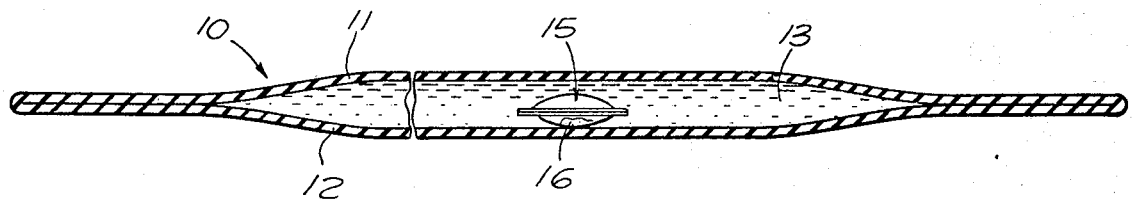
FIG. 2 is a longitudinal cross-sectional view of the shoe insert of FIG. 1.

Reference is now made to FIGS. 1 through 5, inclusive, illustrating a ready-made shoe insert in accordance with the invention, and the manner in which it is used.

A flexible container 10 has an upper wall 11 and a lower wall 12. The walls 11 and 12 are generally parallel to each other; more specifically, however, the upper wall is adapted to approximately conform to the bottom of the foot of the wearer or customer, while the lower wall 12 is adapted to approximately conform to the inner surface of the shoe. Continer 10 is filled with a liquid material 13 which comprises a curable material. Such materials are well-known and include, for example, polyesters and polyurethanes. Such materials are disclosed in U.S. Pat. No. 3,782,390 and U.S. Pat. No. 3,786,580. Curable epoxy resins and silicone rubbers such as Dow Corning RTV (Room Temperature Vulcanizing) silicone rubbers which cure at room temperature may also be used. The curing agents for these are selected catalysts for crosslinking. Also suited for certain uses are the latexes of natural or synthetic rubber. In such cases, the curing agent is a dryer for the latex. Inside the container 10 there is a bulb or inner container 15, which is of relatively small size compared to the container 10. The bulb or inner container 15 is frangible, that is, it is easily fractured or ruptured in response to the application of pressure. Contained within the bulb 15 is a liquid or, perhaps, a powdered material 16 which is a curing or drying agent for the curable material. In chemical terms the material 16 might, therefore, be identified as a catalyst.

Figure 3:
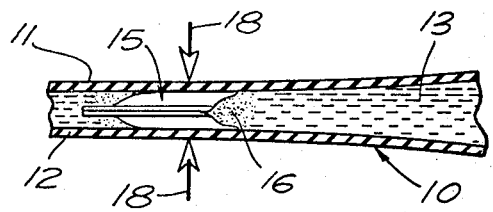
FIG. 3 is a fragmentary cross-sectional view of the shoe insert of FIG. 1.
Figure 5:
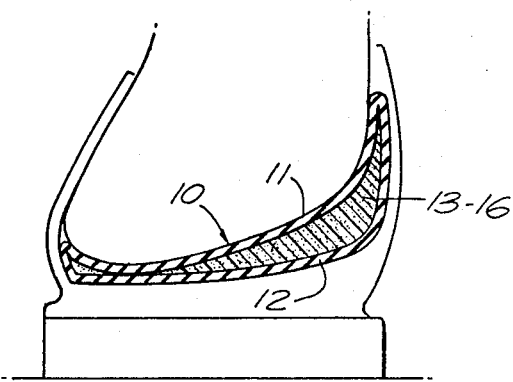
FIG. 5 is a transverse cross-sectional view taken on the line 5—5 of FIG. 4.

Prior to placing container 10 inside the shoe of the wearer it is necessary to rupture the bulb or inner container 15. This is accomplished by applying pressure to both the upper wall 11 and the lower wall 12 of the container 10, as indicated in FIG. 3 by the arrows 18. The result is that bulb or inner container 15 is ruptured and the catalytic material 16 is dispersed into the liquid material 13.

The next step is to perform a mixing or kneading operation which may be accomplished by shaking, twisting, and otherwise manipulating the container 10.

Figure 4:
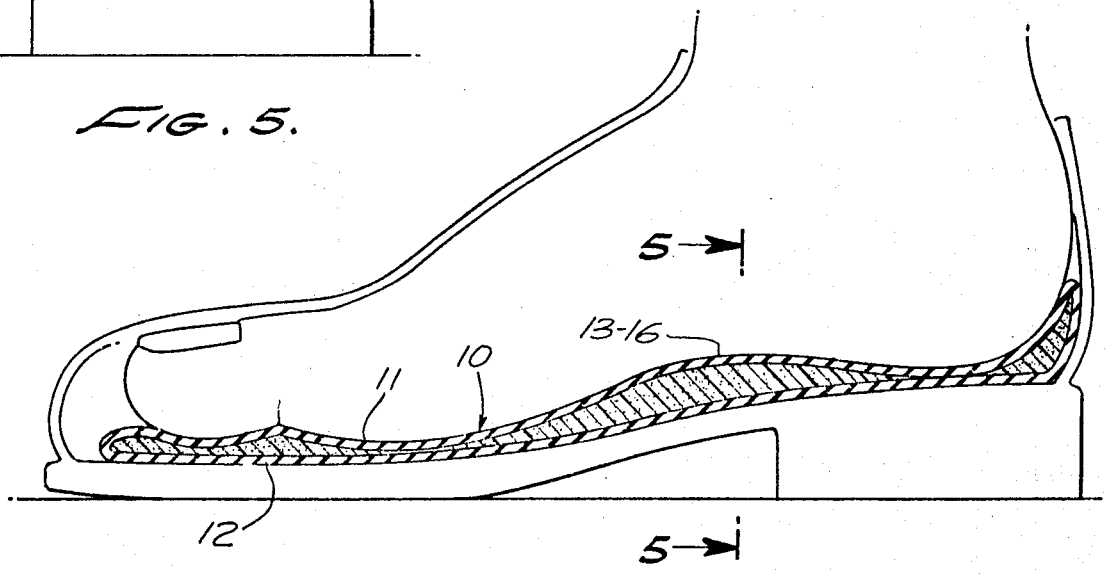
FIG. 4 is an elevational view, partially in cross-section, showing the insert in its operative position between the foot and the shoe of the wearer.

Container 10 is then placed inside the customer's shoe and the customer puts his foot in the shoe as shown in FIG. 4. A downward weight is applied to the customer's foot as previously described while the formable material, now identified by numerals 13–16 to indicate both of its components, completes its setting and curing. The amount of weight applied to the foot is preferably maintained at about a constant level. It is preferred to utilize a selected and properly weighted sandbag, or some other convenient type of auxiliary apparatus, in order to insure that the correct amount of downward force is exerted on each foot and also in order to insure that the amount of downward force is relatively constant while the formable material is setting. Then the device is ready for use by the customer.

The shoe insert as illustrated in FIGS. 1 to 5, inclusive, is of such size as to fit beneath part of or the entire length of the customer's foot and fill part of or the entire length of the shoe. However, essentially the same device may be made in a much smaller configuration so that it fits only into the arch beneath the arch of the foot. The method of constructing the device, and the method of using it, are essentially the same in either application.

Container 10 may be integrally formed from a single material, or the upper and lower walls may be formed of different materials and adhesively secured around their peripheral edge. A flexible leather insole may be affixed to the outside top of the flexible container (in contact with the bottom of the wearer's foot) to absorb perspiration to add comfort in wearing and to ease insertion of the foot into the shoe.

MEASURING APPARATUS

Reference is now made to the drawings, FIGS. 6 through 10, inclusive, which illustrates a measuring apparatus provided in accordance with the present invention.

A flexible container 20, best shown in FIG. 6, is used for measuring the volume or quantity of the filler material that should be used in order to fit the foot of a particular customer with the greatest degree of comfort. Container 20 may, for example, be of the same size and configuration as container 10, so that the volume measurement made by utilizing container 20 and its associated apparatus will directly and precisely indicate the volume or quantity of filler material that should be utilized in the container 10 to provide a cured article that conforms to the arch cavity of the customer. Alternatively, a single container may first be used for measuring, then evacuated and filled with formable material to provide the shoe insert.

Container 20 also has a laterally projecting portion 21 which protrudes laterally outward from the instep portion of the container. A flexible tube 22 is attached to the container extension portion 21.

A pump P controlled by a valve V is utilized for supplying an incompressible liquid through the tube 22 in order to fill the container 20 to the desired level. The pump chamber 32 is filled with the incompressible fluid and the measurement of the volume of fluid used to fill container 20 is made by utilizing a scale 33 provided on the pump marked in arbitrary or standard units (milliliters, ounces, etc.). After this measurement has been made, the flexible container 20 is emptied of the incompressible fluid, e.g., it is evacuated through line 22 by suction applied to line 27 from a vacuum line as explained more fully below. A supply line 25 is utilized for refilling the chamber 32 of pump P to its normal level, i.e., to the zero point.

In actual use, a flexible container 20 is placed in each of the shoes of the customer, and the customer is seated and instructed to place the bottom of his foot on top of the containers 20. Sandbags of a prescribed weight are placed on each knee to maintain a constant weight on the feet. Pump P is then employed to fill the container 20 with the incompressible fluid so that the upper surface of the container is in intimate contact with the bottom of the foot while its lower surface is in intimate contact with the inner bottom surface of the shoe. A reading on the scale 33 is then taken to indicate the volume of fluid injected into container 20. The reading will be that at the maximum advance of plunger 34. The volume determined in this way is then used as a measure of the amount of moldable polymeric material which is used to make the arch support as described herein.

The selection of weight value applied on the customer's foot during the fitting process is most important. If a heavy weight is applied, such as the total weight of the person, the arch of the foot is greatly deflected downward. As a result the volume of filler material required in the insert will be at a minimum, and the supporting action which the shoe insert provides to the arch during normal walking and standing will be at a corresponding minimum. On the other hand, if minimum weight is applied to the foot during fitting, such as one-fourth of the weight of the person, then the amount of filler material required in the shoe insert will be at a maximum. The reason is that the space between shoe and foot is greater. The shoe insert when completed will then provide a corresponding maximum amount of support to the arch of the foot. The selected weight value should be held constant when measuring the required volume of the filler material, and again held constant at the same value when the ready-made shoe insert is being completed by curing the filler material.

The base 41 of the pump has a cylindrical chamber which receives the rotary valve V. The external surface of valve V has an annular groove 45 extending somewhat more than 90 degrees, which receives a screw 42 in order to limit the rotary movement of valve V to a quarter circle. Valve V has a longitudinal central opening 48 which always communicates through a passageway 47 (FIG. 8) with the tube 22. It also has a lateral or vertical opening 49 which has two alternate positions corresponding to the extreme rotary positions of the valve. In the position of valve V as shown in FIGS. 7 and 8 the valve passageway 49 communicates with a vertical passageway 44 in the housing 41. Passageway 44 communicates with a chamber 52 in the lower end of tubular member 51, and a ball type check valve 52 is urged by a spring toward the upper end of chamber 52. Chamber 52, except when closed by valve 53, communicates through a vertical passageway 54 with the pump chamber 32. Pump P has a plunger 34 which is movable vertically relative to the pump housing 31.

It is assumed that initially the chamber 32 of the pump P is filled with liquid to the zero point of the scale 33. The operation of filling the container 20 to the desired volume takes place as follows:

Plunger 34 is moved downward which causes valve 53 to open. Liquid flows from chamber 32 through passageway 54 and chamber 52 into the passageway 44. From there it flows into the valve passage 49 and out the valve passage 48 through passage 47 into tube 22. When the flexible container walls are in intimate contact with both foot and shoe, a reading is taken on the scale 33 of pump P. This intimate contact generally occurs within a pressure range of about one to ten inches of water, and it is preferred to establish this pressure level by means of an automatic pressure regulator, not specifically shown. In any event, the amount of fluid injected is sufficient to fill the arch cavity and, if desired, to inject a small amount under the ball and heel of the foot to provide a cushion.

In order to evacuate the container 20, the valve V is rotated to its alternate position. Valve passage 49 then communicates through passage 43 (FIG. 7) with the vacuum line 27. The contents of container 20 are then withdrawn through the vacuum line 27.

While keeping valve V in its rotated or alternate position as just described, the pump may be refilled. Tubular member 51 has a horizontal passageway 55 which communicates with vertical passageway 54. A chamber 56 is formed at the outer end of passageway 55. A passageway 58 communicates between chamber 56 and the refill tube 25. A ball-shaped valve 57 is supported in chamber 56 and normally closes the passageway 58. As the plunger 34 of pump P is raised, however, check valve 57 opens and liquid is drawn from the tube 25 through passageways 58, 56, 55 and 54 into the pump chamber 32.

When the volume of liquid has been measured as described above, a preformed insert as previously described having that volume of curable material can be selected for use. Alternatively, a custom filled insert can be made by injecting the measured volume into a flexible container as discussed below.

CUSTOM-FILLED INSERT

Reference is now made to the drawings, FIGS. 11 through 16, inclusive, illustrating a custom-filled insert provided in accordance with the present invention.

A flexible container 60 has generally the same configuration as has been shown by the containers 10 and 20. Container 60 is to be filled with a formable material capable of curing to a resilient state. Pump P' contains a quantity of the pre-catalyzed material in liquid form. A tube 62 couples pump P' to the resilient container 60, and the operation of the pump is controlled by a valve V'.

Container 60 is placed inside the shoe of the customer. The downward pressure of the customer's foot is then maintained at a constant level in the manner already described. Container 60 and tube 62 are evacuated through line 67 by turning valve V' to its alternate position.

The valve is then returned to the position shown in FIGS. 12 and 13. The plunger of pump P' is pushed downward in order to fill container 60 with the pre-catalyzed formable material. Preferably pump P' is calibrated so that the volume of material delivered to container 60 can be measured. The amount delivered may, for example, that determined using the measuring apparatus described above. A gage G coupled in communication with the supply line 62 may advantageously be used to control the level of pressure that is applied to the formable material. Initially the material is quite liquid with a rather low viscosity, and may be injected into the container under a rather low pressure. The material then cures and hardens in about ten minutes, in a configuration that is determined by the shapes of both the foot and the shoe.

The pressure level as indicated on gage G is significant when container 60 is first being filled, because at this point of time the filler material has a low viscosity and the pressure measurement is quite meaningful. The optimum level of pressure is of the order of one inch of water where both of the container walls are made of highly flexible material. This amount of pressure is then adequate to provide an intimate contact of the upper wall of container 60 with the bottom surface of the foot, and an intimate contact of the lower wall of the container 60 with the inner surface of the shoe. If the container 60 is made of material having any degree of stiffness, however, a significantly higher level of pressure may be required.

When the formable material has cured, the insert is removed from the customer's shoe and the lateral protrusion 61 is cut off along the dotted line 69, as shown in FIG. 11. The customer now has a completed shoe insert that is ready for his permanent usage.

The cleaning of pump P' may present a problem because of the curing and consequent hardening of the filler material. However, it is possible to construct the pump from plastic materials which are inexpensive and can be thrown away after a single usage.

Still another variation of the invention provides a custom-filled shoe insert without the necessity of evacuating the flexible container. The bottom wall of the container is made of non-porous material whereas the upper wall is made of a material which has a certain degree of porosity, such as leather or synthetic leather or the like. The degree of porosity of the latter material is selected so as to permit entrapped air to escape through it, but not the formable material. Therefore, when the formable material is injected into the container the entrapped air is driven out through the pores of the upper wall.

Figure 17:
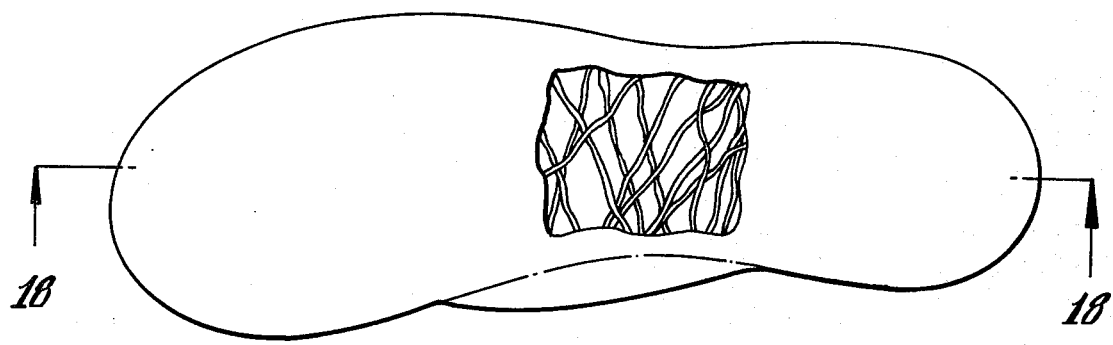
FIG. 17 is a top view of a custom-filled shoe insert having a cutaway portion.

FIG. 17 illustrates yet another ready-made shoe insert employing a preferred feature of the present invention. Shown in FIG. 17 is a flexible container 70 of generally the same construction as containers 10 and 60. Container 70 is similarly filled with a curable material. Plural hollow tubes 72 which contain the curing agent are distributed throughout the container as better seen in FIG. 18.

Preferably, the tubular elements are made of a pliant material that does not break or rupture even with severe handling but which is capable of being converted to frangible material by an embrittling operation. For example, the tubes may be extruded from an uncrosslinked or partially crosslinked polymeric material susceptible of being cured to a frangible state by the action of microwave radiation, ionizing radiation such as gamma radiation, neutrons or high energy electrons, or by the application of heat or other suitable means.

As fabricated, the article can be handled routinely in packaging and shipment. However, just prior to use, the article is exposed to the condition which embrittles the tubular elements. When this operation is complete, the article is manipulated to rupture the tubes and fitting of the insert is accomplished as described in connection with FIG. 1.

Figure 18:
FIG. 18 is a fragmentary cross-sectional view taken on the line 18—18 of FIG. 17.
Figure 19:
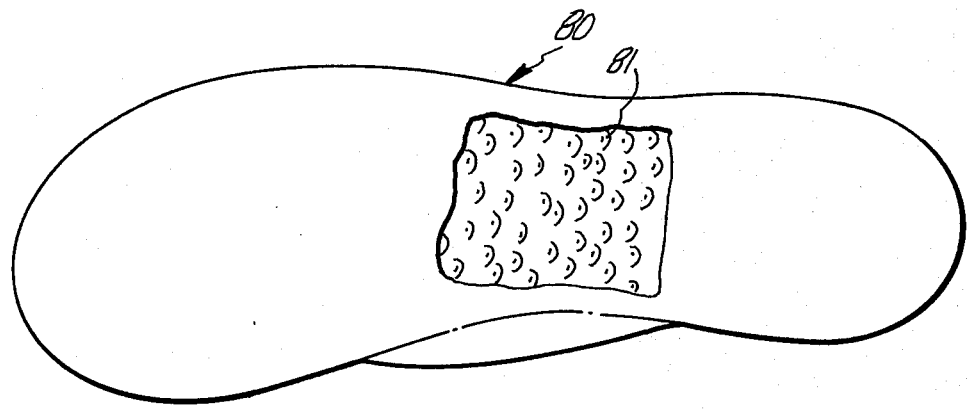
FIG. 19 is a top view of a custom filled shoe insert having a cutaway portion.
Figure 20:
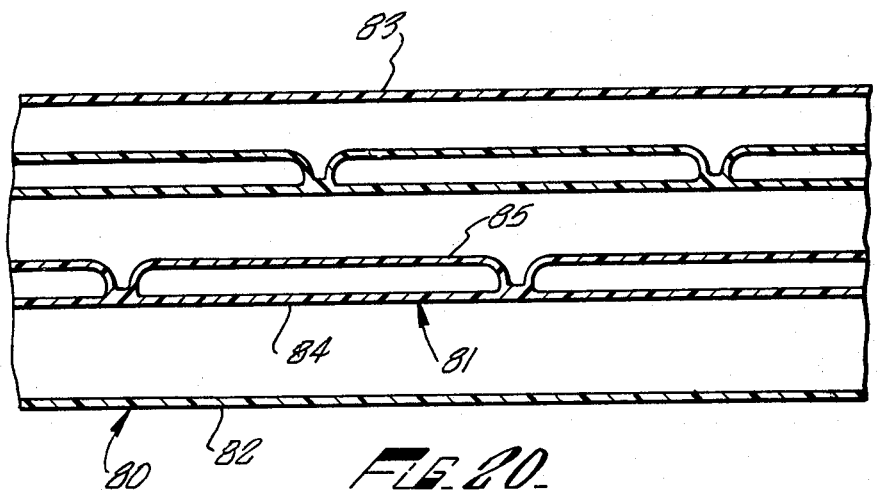
FIG. 20 is a fragmentary transverse cross-section of the insert of FIG. 19.

Yet another refinement of the present invention is shown in FIG. 19 which illustrates a shoe insert of generally the same configuration as that illustrated, for example, in FIG. 1. In FIG. 19 is illustrated a container 80 which is filled with a curable material. The curing agent is carried in frangible nodules or bubbles on a sheet 81. The construction of sheet 81 is better seen in FIG. 20 which illustrates, in partial transverse cross-section, the inserts of FIG. 18. The walls of container 80 is formed by walls 82 and 83. Disposed within the curable material are sheets 81 defined by a layer 84 having plural bubbles 85 disposed thereon. The curing agent is located in the space defined by the bubbles 85 and layer 84. The sheet is frangible and the bubbles can be caused to rupture to release the curing agent by manipulating the sheets.

Preferably the sheet 81 is fabricated initially from a prefrangible material as described in connection with the discussion of FIGS. 17 and 18 to prevent premature rupture of the bubbles during handling. Prior to use, the article is exposed to the operation which embrittles the sheet 81.

The foregoing description has focused on articles in which the curable material and curing agent are contained within a flexible container. However, this expedient may be unnecessary and even undesirable for certain applications. Thus, in another embodiment of the invention, the curable material can be contained within the pores of a foamed polymeric material, for example a foamed elastomer such as a polyurethane. Impregnation of the foam may be accomplished by dipping it in the liquid curable material. Excess liquid is pressed out of the foam which is then sandwiched between two sheets like sheet 81 in FIG. 19 which contain the curing agent. The article may be made from components cut to size or the article can be trimmed to a desired shape after assembly.

In a further embodiment, the article may comprise a coherent mass of flexible fibers. The coherent mass may be formed by weaving a cloth or by twisting or braiding a length to form a cord or rope. Alternatively, the mass may be a simple batting of entangled fibers.

Figure 21:
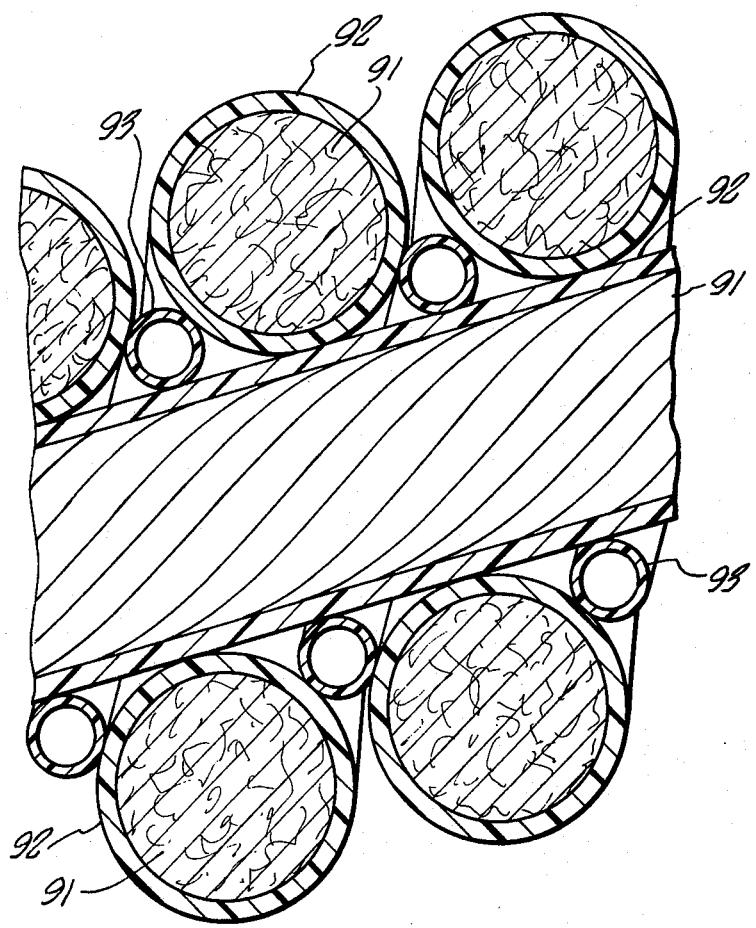
FIG. 21 is a cross-section of a woven material according to the invention.

As fabricated, the largest portion of the fibers will be coated with a viscous curable material. This may be accomplished by dipping the mass in liquid curable material. However, at least a portion of the fibers are hollow tubes of a frangible material containing the curing agent. One such arrangement is shown in FIG. 21, a sectional view of a woven material in which 91 represents a fiber, for example, a natural fiber like cotton or a synthetic fiber such as nylon, coated with a curable material 92. Also woven in the material are hollow tubes 93 of frangible material which contain the curing agent.

The tubes are formed initially of prefrangible material so that the article can be wound or folded for compact storage. Then the article is treated, perhaps by passage through an oven, exposure to microwave radiation or other means to induce further crosslinking to embrittle the tubes containing the curing agent.

When it is desired to use the article, the frangible tubes are ruptured. This can occur during handling by the unwinding or unfolding of the mass or by other suitable manipulation. After the tubes are ruptured, the mass is given a configuration it is desired it retain.

A gauze structure formed in this way could be used to make an orthopedic device which would function like a plaster cast. For example, after setting of a broken bone, an injured limb could be wrapped with the gauze, usually over a protective covering for the limb. When the curable material sets up, the gauze rigidifies and will support the limb as does a conventional cast. Then, if desired, a protection layer may be applied over the gauze. Such a gauze would be porous and, therefore, more comfortable to wear than a plaster cast.

ALTERNATE FORMS

According to the present invention the flexible container 10, 60, 70 or 80 may, if desired, be dismembered and removed so that the cured filler alone may be used as the shoe insert.

According to another variation of the invention a cover member is attached to one surface of the flexible container and becomes a part of the complete shoe insert.

ALTERNATE APPLICATIONS

It should be noted that the technique disclosed herein is not limited to shoe inserts but may also be applied to another body member or to other tangible objects.

SPLINTS, BRACES AND CASTS

The present invention can be utilized for the immobilization of a broken arm or other limb by applying the formable material filled outer container against or around the same until the material cures, whereafter said container can be secured by usual means such as by the use of adhesive or cloth bandages.

MOLDS AND CASTS

Impressions in the form of footprints, human faces, fossils, decorative plaques or other tangible objects can be fabricated for the purpose of making a mold or cast or for maintaining the likeness of the original in a substantially permanent state by the method of the present invention.

The importance of this invention is even more apparent in the area of custom made furniture and prosthetic devices.

Once the catalyst and the formable elastomeric material are united in the outer container in accordance with the procedure as hereinbefore explained, the outer container is comfortably applied to the desired object or portion of the anatomy.

After the curing process is complete, the container is removed from the object, whereupon it is evident that substantially every curve, depression and form of that object has been duplicated onto the container.

From this duplication, the designer is able to custom contour the item of furniture or prosthetic device or other tangible form to the individual specifications of that object, or person, as the case may be. For example, seats for custom made automobiles, space craft or the like could be made by application of the present invention.

The invention has been described in considerable detail in order to comply with the patent laws by providing a full public disclosure of at least one of its forms. However, such detailed description is not intended in any way to limit the broad features or principles of the invention, or the scope of patent monopoly to be granted.

I claim:

1. An article comprising a mass of coherent fibers, said mass comprising, as a first portion, fibers having a curable substance coated thereon and, as a second portion, pliant hollow fibers uniformly dispersed in said coated fibers and being capable of being rendered frangible, said hollow fibers containing a curing agent for said curable substance.

2. An article according to claim 1 wherein said mass comprises woven fibers.

3. An article according to claim 1 wherein said mass comprises twisted fibers.

4. An article according to claim 1 wherein said mass comprises braided fibers.

5. An article according to claim 1 wherein said mass comprises a batting of fibers.

6. The article of claim 1 wherein the mass is enclosed in a flexible container.

7. An article according to claim 6, adapted by size and shape to be inserted into a shoe and to serve as an insole.

* * * * *